United States Patent [19]

Imanari et al.

[11] Patent Number: 4,937,392

[45] Date of Patent: Jun. 26, 1990

[54] PROCESS FOR PREPARING 4,4'-DIHYDROXYDIPHENYLMETHANE

[75] Inventors: Makoto Imanari; Hiroshi Iwane; Takahiro Sugawara; Satoshi Ohtaka; Naoki Suzuki, all of Ibaraki, Japan

[73] Assignee: Mitsubishi Petrochemical Company, Ltd., Tokyo, Japan

[21] Appl. No.: 317,956

[22] Filed: Mar. 2, 1989

[30] Foreign Application Priority Data

Mar. 4, 1988 [JP] Japan ............................ 63-51240

[51] Int. Cl.$^5$ ................. C07C 37/20; C07C 39/16
[52] U.S. Cl. .......................... 568/727; 568/722; 568/724
[58] Field of Search ............. 568/724, 722, 727, 728

[56] References Cited

U.S. PATENT DOCUMENTS

| 3,073,868 | 1/1963 | Prahl et al. | 568/724 |
| 4,294,993 | 10/1981 | Li | 568/724 |

FOREIGN PATENT DOCUMENTS

| 249171 | 9/1960 | Australia | 568/728 |
| 1051864 | 11/1953 | Belgium . | |
| 0109033 | 5/1984 | European Pat. Off. | 568/724 |
| 1153763 | 9/1963 | Fed. Rep. of Germany | 568/724 |
| 1362968 | 12/1964 | France | 568/724 |
| 8202565 | 2/1983 | Netherlands | 568/724 |
| 176261 | 7/1963 | U.S.S.R. | 568/724 |
| 891800 | 8/1959 | United Kingdom | 568/724 |
| 1111874 | 1/1967 | United Kingdom | 568/724 |
| 1410750 | 5/1974 | United Kingdom | 568/724 |

*Primary Examiner*—Werren B. Lone
*Attorney, Agent, or Firm*—Oblon, Spivak, McClelland, Maier & Neustadt

[57] ABSTRACT

A process for preparing 4,4'-dihydroxydiphenylmethane, which comprises reacting phenol with formaldehyde in the presence of an acidic catalyst and separating the aimed 4,4'-dihydroxydiphenylmethane from the crude dihydroxydiphenylmethane thus obtained, is disclosed. According to this process, 4,4'-dihydroxydiphenylmethane can be separated from its isomers and oligomers at a high purity and at a high yield, compared with those achieved by known methods. Thus highly useful 4,4'-dihydroxydiphenylmethane can be advantageously prepared on an industrial scale.

5 Claims, No Drawings

PROCESS FOR PREPARING 4,4'-DIHYDROXYDIPHENYLMETHANE

FIELD OF THE INVENTION

This invention relates to a process for preparing 4,4'-dihydroxydiphenylmethane which comprises reacting phenol with formaldehyde in the presence of an acidic catalyst and separating isomers from the crude dihydroxydiphenylmethane thus obtained.

4,4'-Dihydroxydiphenylmethane is highly useful as a starting material for the preparation of epoxy resins, polyester resins and polycarbonate resins as well as a modifier and a stabilizer for phenol resins.

BACKGROUND OF THE INVENTION

Known methods for preparing dihydroxydiphenylmethane are as follows:

(1) a method comprising reacting phenol with dimethylol urea in the presence of an acidic catalyst and extracting the aimed dihydroxydiphenylmethane from the resulting product followed by recrystallization from water (cf. U.S. Pat. Ser. No. 2,617,832);

(2) a method comprising reacting phenol with formaldehyde and then silylating the resulting product followed by fractional distillation and desylilation (cf. U.S. Pat. Ser. No. 2,804,480);

(3) a method comprising reacting phenol with formaldehyde in dimethylformamide (DMF) [cf. JP-B-4838694 (The term "JP-B" as used herein means an "examined Japanese patent publication")]; and (4) a method comprising reacting phenol with formaldehyde in the presence of urea, filtering the solid thus precipitated and recrystallizing the same from water (cf. JP-B-39-26844).

A reaction between phenol and formaldehyde in the presence of an acidic catalyst would generally give 10 to 25% by weight of 2,2'-dihydroxydiphenylmethane, which will be abbreviated as 2,2'-BPF hereinafter, 40 to 60% by weight of 2,4'-dihydroxydiphenylmethane, which will be abbreviated as 2,4'-BPF hereinafter, 25 to 40% by weight of 4,4'-dihydroxydiphenylmethane, which will be abbreviated as 4,4'-BPF hereinafter, and oligomers such as trimers, tetramers and higher ones, the total of 2,2'-BPF, 2,4'-BPF, 4,4'-BPF and oligomers being 100% by weight. No process for selectively synthesizing 4,4'BPF alone has been developed so far. Recently the demand for 4,4'-BPF has been more and more increasing. Therefore it is required to divide crude dihydroxydiphenylmethane, i.e., a mixture of 2,2'-BPF, 2,4'-BPF, 4,4'-BPF and oligomers, which will be abbreviated as BPF hereinafter, on an industrial scale.

However the above method (1) is disadvantageous from an industrial viewpoint, since the dimethylol urea employed as a starting material is unstable; the recrystallization from water gives only a limited yield; and the recovery of the phenol contained in the water, which is required during the course of the treatment of the waste, is not always easy. The method (2) is also disadvantageous from an industrial viewpoint, since it requires an expensive silylating agent. The selectivity of 4,4'-BPF established by the method (3) is somewhat improved but not yet sufficient. Further it is required in this method to recover the phenol as well as the expensive solvent. Furthermore, it is not shown whether highly pure 4,4'-BPF can be obtained or not, though a purification step, i.e., recrystallization is described. The method (4) is essentially similar to the method (1) and thus it is also disadvantageous from an industrial viewpoint. Thus none of these known methods enables the advantageous preparation of 4,4'-BPF on an industrial scale.

SUMMARY OF THE INVENTION

The inventors of the present invention have attempted to solve the abovementioned problems by establishing a process for the advantageous preparation of 4,4'-BPF on an industrial scale by separating the aimed 4,4'-BPF from its isomers, thus completing the present invention.

Accordingly, the present invention provides a process for advantageously preparing 4,4'-BPF of a high purity at a high yield on an industrial scale from a BPF mixture, which is obtained by reacting phenol with formaldehyde in the presence of acidic catalyst, through recrystallization, which has been considered difficult hitherto.

The present invention provides a process for separating dihydroxydiphenylmethane isomers which comprises treating a crude dihydroxydiphenylmethane, which is obtained by reacting phenol with formaldehyde in the presence of an acidic catalyst and then removing the unreacted phenol, with an aromatic hydrocarbon as well as a process for obtaining highly pure 4,4'-dihydroxydiphenylmethane thereby.

The process of the present invention has many advantages, for example:

(1) it gives highly pure 4,4'-BPF at a high yield even from a BPF mixture, which contains 4,4'-BPF at a content as low as 25 to 40% by weight, through single recrystallization;

(2) it is accompanied by no waste treatment since no water is employed in the separation procedure; and (3) it can be completed in a single solvent system, which facilitates the recovery and reuse of the solvent.

DETAILED DESCRIPTION OF THE INVENTION

BPF

The BPF to be used in the present invention may be the residue obtained by subjecting formaldehyde to addition condensation with an excessive amount of phenol in the presence of an acidic catalyst and distilling off the unreacted phenol. As a matter of course, the 4,4'BPF content of the starting BPF may be elevated to a certain degree by adding the third component, for example, urea thereto. The residue is viscous and would not solidify in general unless, for example, kneaded. Either a viscous BPF or a solidified one may be used in the present invention.

When no third component is added, the BPF is present as a mixture comprising 10 to 25% by weight of 2,2'-BPF, 40 to 60% by weight of 2,4'-BPF, 25 to 40% by weight of 4,4'-BPF and oligomers involving trimers and higher ones, the total of 2,2'-BPF, 2,4'-BPF, 4,4'-BPF and oligomers being 100% by weight. It is needless to say, however, a BPF comprising an elevated content of 4,4'-BPF and lower contents of the isomers and oligomers is preferable.

There have been known a number of methods for preparing BPF by reacting phenol with formaldehyde. Examples thereof include a method wherein an inorganic liquid acid such as hydrochloric acid, sulfuric acid or phosphoric acid is used as a catalyst (cf. JP-A-58-177928 (The term "JP-A" as used herein means an "unexamined published Japanese patent application"); British Patent No. 1,493,759 and U.S. Pat. Ser. No. 2,792,429) and one wherein oxalic acid is used as an acid catalyst (cf. JP-A-55-124730).

In addition, there is known a process for synthesizing BPF with the use of a solid acid, i.e., alumino silicate (cf. U.S. Pat. Ser. No. 3,496,239). In each of these methods, 10% by weight or more of oligomers including trimers and higher ones are formed as side-products regardless of the employed acid, unless the phenol and formaldehyde are employed at a molar ratio of 25:1 or above.

When activated clay, which is obtained by chemically treating a montmorillonite clay (acid clay), is used as a catalyst, the content of the oligomers including trimers and higher ones in the obtained reaction product amounts to 10% by weight or below, even if the molar ratio between the phenol and formaldehyde is around 20:1. Thus the latter process is preferable for preparing BPF according to the present invention.

In the process of the present invention wherein activated clay is used, the activated clay may be employed in an amount of 0.05 to 10% by weight, preferably 0.2 to 3.0% by weight, based on the phenol. An amount of the activated clay less than 0.05% by weight is unpreferable since the reaction would not sufficiently proceed in this case. When it exceeds 10% by weight, on the other hand, no advantage can be achieved any more. Thus it is undesirable from an economical viewpoint.

The reaction may be carried out, in general, by heating and stirring an aqueous solution of formaldehyde, phenol and activated clay in the presence of an inert gas under atmospheric pressure. In addition to the abovementioned aqueous solution, various formaldehyde sources including cyclic polymers such as trioxane and tetraoxane and chain polymers such as paraformaldehyde may be used therefore. It is sometimes possible to add 5 to 50% by weight, based on the above-mentioned polymer, of water to the reaction system.

Although the molar ratio between the phenol and formaldehyde may be 3:1 or above, a molar ratio of 20:1 or above, still preferably 20:1 to 25:1, is preferable in order to lower the content of the oligomers including trimers and higher ones to a level of 10% by weight or below. A molar ratio exceeding 25:1 is undesirable, since the yield is lowered in this case.

Examples of the inert gas include nitrogen, argon, helium, hydrogen and carbon dioxide gases. Either one of these gases or a mixture thereof may be used in this process. When the reaction is carried out in the absence of any inert gas, the BPF might be undesirably colored.

The reaction may be carried out at a temperature of 20° to 110° C, preferably 40° to 90° C. When the reaction temperature is lower than 20° C, the reaction would proceed at a considerably low rate and thus require a long time for the completion, which is undesirable in practice. When it exceeds 110° C, on the other hand, the content of the oligomers including trimers and higher ones is increased, which is undesirable.

From the reaction mixture thus obtained, the unreacted phenol is distilled off. The obtained residue may be preferably used as the starting BPF in the process of the present invention.

Solvent

The solvent to be used in the present invention may be selected from among aromatic hydrocarbons, e.g., benzene and alkylbenzenes obtained by substituting one to three hydrogen atoms of benzene with alkyl group(s). Although the substitution positions on benzene may be arbitrarily selected, these substituents preferably carry one to four carbon atoms in all. Examples of the solvent include toluene, ethylbenzene, cumene, o-xylene, m-xylene, p-xylene, o,m,p-xylene mixture, pseudocumene and mesitylene. Among these solvents, benzene, toluene, xylene, ethylbenzene and cumene are preferable, since they can be commercially available, inexpensive and readily recovered. Although solvent mixtures obtained by, for example, adding methanol, acetone, acetic acid or diisopropyl ether to an aromatic hydrocarbon may be used in the process of the present invention, they are not advantageous from an industrial viewpoint. This is because they require troublesome procedures for recovery and reuse.

Separation

In the case of recrystallization, 1 to 20 parts, preferably 5 to 15 parts, of an aromatic hydrocarbon is added per part of the BPF. This procedure may be carried out at any temperature without limitation. However the BPF may be generally heated to the boiling point of the solvent and thus dissolved therein. Then the solution is allowed to cool down to room temperature. Thus 4,4'-BPF would crystallize out at a high purity. Although a single recrystallization can give a sufficiently high purity of the 4,4'-BPF, the purity can be further elevated by repeating the recrystallization.

The separation by washing is similar to that by recrystallization, in principle. Namely, 4,4'-BPF can be a separated from 2,2'-BPF, 2,4'-BPF and oligomers by taking advantage of the difference in the solubilities thereof in an aromatic hydrocarbon. In this case, it is preferable that the starting BPF is solidified and then ground. The washing temperature may be 40 to 100° C, preferably 50 to 80° C. After the washing, the washing liquor may be filtered at a high temperature to thereby give 4,4'-BPF of a high purity.

The residue is rich in 2,4'-BPF and 2,2'-BPF. When it is used as a starting material for preparing epoxy resins, these epoxy resins give a characteristic suitable for civil uses, which would hardly crystallizes and have a high workability.

To further illustrate the present invention, the following Examples will be given, wherein a BPF-yield, a yield and a purity are defined according to the following formula, respectively, based on the results of the analysis by liquid chromatography.

$BPF$ yield (%) =

Formed $BPF$ (mol)/Used formaldehyde (mol) × 100

Yield (%) = $\frac{\text{Weight of isolated and purified } 4,4'\text{-}BPF}{\text{Weight of } 4,4'\text{-}BPF \text{ in starting } BPF}$ × 100

Purity (%) = $\frac{\text{Weight of contained } 4,4'\text{-}BPF}{\text{Weight of analyzed sample}}$ × 100

REFERENTIAL EXAMPLES 1 to 4

To a 50 ml short-necked flask, were added 18.82 g (200 mmol) of phenol, 0.19 g (1.0% by weight based on the phenol) of activated clay (Gareon Earth V₂; mfd. by Mizusawa Kagaku Kogyo K.K.) and a definite amount (cf. Table 1) of a 37% by weight aqueous solution of formaldehyde. The resulting mixture was stirred at 80° C under a nitrogen atmosphere for two hours. After filtering the catalyst, a colorless and transparent reaction mixture was obtained. The unreacted phenol and oligomers including trimers and higher ones contained in the reaction mixture were determined by high performance liquid chromatography of internal standard method. Table 1 shows the results.

TABLE 1

| Referential Example | PL/FA* (molar ratio) | PL conversion ratio (%) | BPF composition 2,2'-isomer | BPF composition 2,4'-isomer | BPF composition 4,4'-isomer | BPF yield (FA base, %) | Content of trimer and higher ones (% by weight) |
|---|---|---|---|---|---|---|---|
| 1 | 8.0 | 24.5 | 17.1 | 41.4 | 44.5 | 63.1 | 22.6 |
| 2 | 15.0 | 14.4 | 17.0 | 41.3 | 41.7 | 75.4 | 14.1 |
| 3 | 20.0 | 9.0 | 16.5 | 42.6 | 40.9 | 81.6 | 9.3 |
| 4 | 25.0 | 7.8 | 16.7 | 40.5 | 42.8 | 89.5 | 8.1 |

PL: phenol.
FA: formaldehyde.

REFERENTIAL EXAMPLES 5 to 8

To a 50 ml short-necked flask, were added 18.82 g (200 mmol) of phenol, 0.06 g (0.3% by weight based on the phenol) of oxalic acid dihydrate and a definite amount (cf. Table 2) of a 37% by weight aqueous solution of formaldehyde. The resulting mixture was stirred at 80° C under a nitrogen atmosphere for two hours. Thus a colorless and transparent reaction mixture was obtained. Table 2 shows the results.

TABLE 2

| Referential Example | PL/FA* (molar ratio) | PL conversion ratio (%) | BPF composition 2,2'-isomer | BPF composition 2,4'-isomer | BPF composition 4,4'-isomer | BPF yield (FA base, %) | Content of trimer and higher ones (% by weight) |
|---|---|---|---|---|---|---|---|
| 5 | 12.0 | 18.4 | 18.1 | 48.5 | 33.4 | 67.5 | 19.4 |
| 6 | 18.0 | 11.1 | 19.9 | 50.3 | 29.8 | 76.1 | 13.6 |
| 7 | 20.5 | 8.7 | 19.5 | 49.2 | 31.3 | 78.9 | 11.8 |
| 8 | 25.0 | 7.3 | 20.6 | 49.9 | 29.5 | 81.4 | 9.4 |

REFERENTIAL EXAMPLE 9

To a 50 ml short-necked flask, were added 18.82 g (200 mmol) of phenol, 0.65 g (3.5% by weight based on the phenol) of concentrated hydrochloric acid and 0.81 g (10.0 mmol) of a 37% by weight aqueous solution of formaldehyde. The resulting mixture was stirred at 80° C under a nitrogen atmosphere for two hours. Thus a red and transparent reaction mixture was obtained. After neutralizing the reaction mixture with an aqueous solution of sodium hydroxide, the oily phase was analyzed. As a result, the phenol conversion ratio was 8.5%, the yield of the dimers on an FA base was 77.9% and the content of oligomers including trimers and higher ones was 12.3% by weight. The bis(hydroxyphenyl)methane mixture comprised 15.3% by weight of 2,2'-isomer, 48.3% by weight of 2,4'-isomer and 36.4% by weight of 4,4'-isomer.

EXAMPLE 1

940 g (10 mol) of phenol was reacted with 15 g (0.5 mol) of formaldehyde in the presence of 10 g of activated clay at 80° C for two hours. Then the activated clay was filtered off from the resulting reaction mixture. After distilling off the unreacted phenol, 180 g of a residue was obtained. The crude BPF thus obtained, which was in the form of a viscous syrup, showed the following composition.

Composition

| Component | Content (% by weight) |
|---|---|
| 2,2'-BPF | 15.8 |
| 2,4'-BPF | 38.4 |
| 4,4'-BPF | 38.8 |
| Oligomer | 7.0 |

10 g of the crude BPF thus obtained was dissolved in 100 cc of ethylbenzene under refluxing and then cooled to room temperature. The crystals thus precipitated were filtered and dried to thereby give 3.4 g of a product. As the result of liquid chromatographic analysis, the product contained 97.2% by weight of 4,4'-BPF, together with 1.9% by weight of 2,4'-BPF, 0.8% by weight of 2,2'-BPF and 0.1% by weight of oligomers and the yield of the 4,4'-BPF was 88.2%.

On the other hand, the residue contained 7.1% by weight of 4,4'-BPF, 58.3% by weight of 2,4'-BPF, 24.0% by weight of 2,2'-BPF and 10.6% by weight of oligomers.

EXAMPLE 2

2 g of the 4,4'-BPF obtained in Example 1 was treated in the same manner as the one described in Example 1 by using 10 g of ethylbenzene. As a result, 4,4'-BPF was obtained at a purity of 99.7% and at a yield of 99.3%.

EXAMPLE 3

30 g of the crude BPF obtained in Example 1 was solidified by kneading and then ground. 10 g of the BPF powder thus obtained, which had the same composition as the one shown in Example 1, was suspended in 100 cc of toluene and stirred at 60° C for one hours. After filtering at a high temperature, the resulting solid was dried. Thus 4,4'-BPF was obtained at a purity of 95.2% and at a yield of 83.1%.

COMPARATIVE EXAMPLE 1

10 g of the crude BPF thus obtained in Example 1 was dissolved in 10 cc of isopropyl ether under refluxing and then recrystallized. Thus 4,4'-BPF was obtained at a purity of 76.0% and at a yield of 55.3%.

On the other hand, the residue contained 33.4% by weight of 4,4'-BPF, 40.9% by weight of 2,4'-BPF, 17.7% by weight of 2,2'-BPF and 8.0% by weight of oligomers.

COMPARATIVE EXAMPLE 2

The same recrystallization as the one described in Comparative Example 1 was carried out except using 10cc of methyl isobutyl ketone (MIBK). As a result, 4,4'-BPF was obtained at a purity of 77.9% and at a yield of 39.9%.

COMPARATIVE EXAMPLE 3

To 10 g of the crude BPF obtained in Example 1, was added 500 cc of water. Although the mixture was heated under refluxing, the BPF was not dissolved. The aqueous phase was decanted and cooled and then crystals were precipitated. Thus 4,4'-BPF was obtained at a yield of 14.8% and at a purity of 96.2%. The residue contained 35.2% by weight of 4,4'-BPF. Table 3 shows the results.

TABLE 3

|  | Example 1 | Example 2 | Example 3 | Comparative Example 1 | Comparative Example 2 | Comparative Example 3 |
|---|---|---|---|---|---|---|
| Solvent | ethylbenzene | ethylbenzene | toluene | isopropyl ether | MIBK | water |
| Yield (%) | 88.2 | 99.7 | 83.1 | 55.3 | 39.9 | 14.8 |
| Purity (%) | 97.2 | 99.3 | 95.2 | 76.0 | 77.9 | 96.2 |
| Remarks |  | 2nd recrystallization of Example 1 | Washing |  |  | Not completely dissolved |

Table 3 indicates that each process of the present invention is significantly superior to those wherein other solvents are used.

While the invention has been described in detail and with reference to specific embodiments thereof, it will be apparent to one skilled in the art that various changes and modifications can be made therein without departing from the spirit and scope thereof.

What is claimed is:

1. A process for preparing 4,4'-dihydroxydiphenylmethane, which comprises:
   reacting phenol with formaldehyde at a molar ratio ranging from 20:1 to 25:1 in the presence of acidic activated clay catalyst at a temperature ranging from 20° to 110° C;
   removing the unreacted phenol from the resulting reaction mixture; and
   recrystallizing the crude dihydroxydiphenylmethane thus obtained from benzene or an alkylbenzene whose substituent(s) carries 1–4 carbon atoms in all.

2. The process of claim 1, wherein said crude dihydroxydiphenylmethane contains 4,4'-dihydroxydiphenylmethane and 2,2'- and 2,4'-isomers of 4,4'-dihydroxydiphenylmethane.

3. The process of claim 1, wherein said aromatic hydrocarbon is employed in an amount of 1 to 20 parts by weight per part by weight of said crude dihydroxydiphenylmethane.

4. The process of claim 1, wherein said alkylbenzene is toluene, ethylbenzene, cumene, 0-xylene, m-xylene, p-xylene, mixtures of the xylene isomers, pseudocumene or mesitylene.

5. The process of claim 4, wherein said aromatic solvent is benzene, toluene, xylene, ethylbenzene or cumene.

* * * * *